United States Patent [19]

Jöensson et al.

[11] 4,218,476
[45] Aug. 19, 1980

[54] ANTI-THROMBOTIC N-ALKYLTHIOAKYLAMINO BENZENESULFONAMIDES

[75] Inventors: Åake N. Jöensson, Solna; Ferenc Mérenyi, Taeby; Pinchas Moses, Saltsjoe-Boo; Lennart E. Karlsson, Vaellingby; Gunnar Hanshoff, Jaerfaella, all of Sweden

[73] Assignee: AB Kabi, Stockholm, Sweden

[21] Appl. No.: 930,614

[22] Filed: Aug. 3, 1978

[30] Foreign Application Priority Data

Aug. 5, 1977 [GB] United Kingdom ............... 32946/77

[51] Int. Cl.² .................. C07C 143/76; C07C 143/78; A61K 31/18; A61K 31/63
[52] U.S. Cl. ............... 424/321; 260/556 A; 260/556 B; 260/556 AR; 260/397.7 R; 424/228
[58] Field of Search ........ 260/556 A, 556 B, 556 AR, 260/397.7 R; 424/321, 228

[56] References Cited

U.S. PATENT DOCUMENTS

| 3,895,010 | 7/1975 | Goralski et al. | 260/556 A X |
| 4,069,254 | 1/1978 | Hidaka et al. | 260/556 AR |
| 4,098,889 | 7/1978 | Dunbar | 424/321 X |

Primary Examiner—Thomas A. Waltz
Attorney, Agent, or Firm—Pollock, Vande Sande & Priddy

[57] ABSTRACT

New compounds of the general formula I

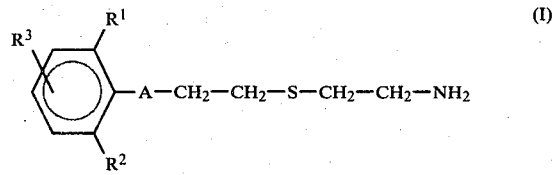

wherein $R^1$ and $R^2$ each independently represent an alkyl group containing 1 to 4 carbon atoms, or an alkoxy group containing 1 to 3 carbon atoms, or halogen, $R^3$ represents hydrogen, halogen, an alkyl group containing 1 to 4 carbon atoms, an alkoxy group containing 1 to 3 carbon atoms, an amino group or a nitro group, A represents

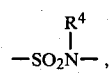

which is bonded to the benzene ring by its sulphur or nitrogen atom and in which $R^4$ is hydrogen or an alkyl group containing 1 to 4 carbon atoms; together with salts thereof with physiologically acceptable acids and, when $R^4$ is hydrogen, with physiologically acceptable bases are described. The compounds are of use in inhibiting thrombosis formation, in treating thrombosis and in fibronolytic therapy. Various methods of producing the new compounds are described involving the building up of the $-A-CH_2-CH_2-S-CH_2CH_2NH_2$ side chain from aromatic precursors having an incomplete side chain or by introducing at least one of the $R^1$, $R^2$ or $R^3$ substituents into a precursor lacking that substituent or from an amino-protected precursor.

18 Claims, No Drawings

ANTI-THROMBOTIC N-ALKYLTHIOAKYLAMINO BENZENESULFONAMIDES

DESCRIPTION

TECHNICAL FIELD

This invention relates to new di-ortho substituted benzenes, to methods for their production, to pharmaceutical compositions containing them and to their use in inhibiting the activity of Factor XIII (fibrinoligase) in blood.

BACKGROUND TO THE INVENTION

When blood is coagulated, the water soluble protein fibrinogen is converted to an insoluble gel of aggregated fibrin molecules. This gel, which is mechanically weak, is easily broken down by proteolytic enzymes. In the presence of Factor XIII (fibrinoligase), as in normal blood and plasma, the fibrin gel is converted to cross-linked, insoluble and mechanically stable fibrin, which is considerably more resistant to proteolytic enzymes than the fibrin gel. If Factor XIII activity is inhibited, the fibrin remains in its non-crosslinked, easily dissolvable form, and in this manner the formation of thrombosis is counteracted. Physiologically acceptable inhibitors of Factor XIII are therefore of great therapeutical interest.

It is known that certain compounds containing a primary amino group and an aryl group can act as competitive inhibitors of Factor XIII; see e.g. L. Lorand & L. G. Nilsson, Molecular Approach for Designing Inhibitors to Enzymes Involved in Blood Clotting in Drug. Design, Vol. 3, E. J. Arens, editor, Academic Press, N. Y. 1972. One example of this type of compound is danslylcadaverine, having the following structure:

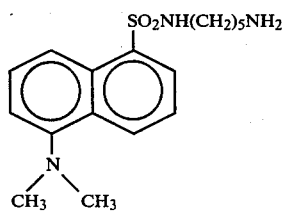

Dansylcadaverine and the corresponding analogue having a 3-thiapentane side chain have proved to be rather active. It is, however, also known that naphthylamines can be highly carcenogenic, and it is not advisable to use naphthylamino compounds as drugs, especially drugs being administered for a long period of time. Great efforts have been made to find alternative, toxicologically acceptable compounds having the same or better activity than these naphthalene derivatives, but so far without success. It should be noticed in this connection that corresponding compounds containing an optionally substituted benzene ring, instead of the napthalene ring, have been tested and found to present such low activities that they were considered to be of no therapeutic interest.

It has now surprisingly been found that compounds of formula (I) below, containing a diorthosubstituted benzene ring, are considerably more active than the known benzene derivatives, while at the same time are more acceptable from the toxicological viewpoint, than to the above mentioned naphthylamine derivatives.

DETAILED DESCRIPTION OF THE INVENTION

The present invention provides a new di-orthosubstituted benzene compound characterised in that it has the general formula (I)

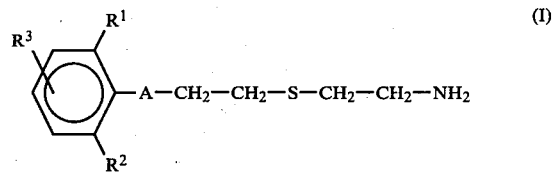

wherein $R^1$ and $R^2$ each independently represent an alkyl group containing 1 to 4 carbon atoms, or an alkoxy group containing 1 to 3 carbon atoms, or halogen, $R^3$ represents hydrogen, halogen, an alkyl group containing 1 to 4 carbon atoms, an alkoxy group containing 1 to 3 carbon atoms, an amino group or a nitro group, A represents

which is bonded to the benzene ring by its sulphur or nitrogen atom and in which $R^4$ is hydrogen or an alkyl group containing 1 to 4 carbon atoms; together with salts thereof with physiologically acceptable acids and, when $R^4$ is hydrogen, with physiological acceptable bases.

When $R^1$, $R^2$, $R^3$ or $R^4$ is an alkyl group, this alkyl group can be straight or branched, e.g. methyl, ethyl, n-propyl, isopropyl or tert.-butyl. The substituent $R^3$ may be in the meta or, preferably, the para position on the benzene ring. The sulphonamide group

is bonded to the benzene ring either by its nitrogen or, preferably, by its sulphur atom.

Particularly active compounds of the invention are those in which group A is linked to the benzene ring directly via its sulphur atom, $R^4$ is H, the two di-ortho substituents are each methyl and $R^3$ is H or a para methyl, propyl or butyl group, preferred compounds including N-(5-amino-3-thiapentyl)-2,6-dimethylbenzene sulphonamide, N-(5-amino-thiapentyl)-2,4,6-trimethylenzene sulphonamide, N-(5-amino-3-thiopentyl)-2,6-dimethyl-5-isopropylbenzene sulphonamide and N-(5-amino-3-thiapentyl)-2,6-dimethyl-b 4-tert.-butylbenzene sulphonamide.

The compounds of the invention may be presented as salts with any of the physiologically acceptable acids customarily used in therapy e.g. as the hydrochloride, phosphate, citrate, tartrate or, when $R^4$ is hydrogen, with any of the physiologically acceptable bases customarily used in therapy e.g. with sodium hydroxide, ammonium hydroxide, aluminium hydroxide or nontoxic amines such as triethylamine. References in this specification to compounds of formula I includes references to salts thereof unless the context requires otherwise.

The invention also relates to methods for preparing the new compounds of formula (I). The methods involve (a) synthesising the side chain —A—CH$_2$—CH$_2$—S—CH$_2$—CH$_2$—NH$_2$ by a method known per se in an aromatic precursor of a formula I compound in which the side chain is incomplete.

(b) introducing, by a method known per se, at least one of the groups R$^1$, R$^2$ or R$^3$ into an aromatic precursor of a formula I compound lacking at least one of the groups R$^1$, R$^2$ or R$^3$, or (c) releasing the terminal amino group by a method known per se, from an aromatic precursor of a formula I compound having a protected terminal amino group.

More specifically, the compounds may be prepared by one of the following methods.

(a) reacting a compound of formula (II)

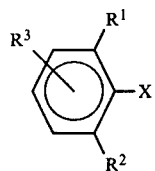
(II)

wherein R$^1$, R$^2$ and R$^3$ are as defined above and X signifies —SO$_2$Hal or

with a compound of formula (III)

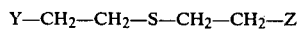
Y—CH$_2$—CH$_2$—S—CH$_2$—CH$_2$—Z    (III)

wherein Z is a free or protected amino group and Y signifies -SO$_2$Hal or

Y being -SO$_2$Hal when X is

and vice versa, and then splitting off any amino protecting group present.

(b) reacting a compound of formula (IV)

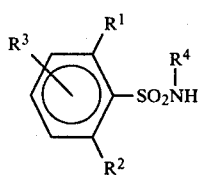
(IV)

wherein R$^1$, R$^2$, R$^3$ and R$^4$ are as defined above, with a compound of formula (V)

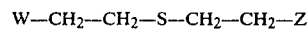
W—CH$_2$—CH$_2$—S—CH$_2$—CH$_2$—Z    (V)

wherein Z is as defined above and W represents a reactive leaving group and then splitting off any amino protecting group present;

(c) reacting a compound of formula (VI)

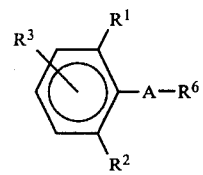
(VI)

ps wherein R$^1$, R$^2$, R$^3$ and A are as defined above and R$^6$ represents the group —CH$_2$—CH$_2$—W, wherein W is as defined above, or, when the nitrogen of A is bonded to the benzene ring, the group —CH=CH$_2$, with a compound of formula (VII)

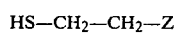
HS—CH$_2$—CH$_2$—Z    (VII)

wherein Z is as defined above, and then splitting off any amino protecting group present;

(d) reacting a compound of formula (VIII)

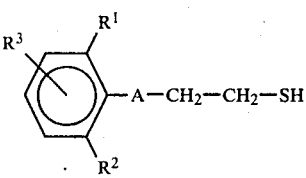
(VIII)

wherein R$^1$, R$^2$, R$^3$ and A are as defined above, with aziridine

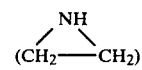

or a compound W—CH$_2$—CH$_2$—Z, wherein Z and W are as defined above, and then splitting off any amino protecting group present;

(e) reducing a compound of formula (IX)

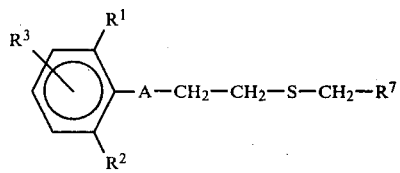
(IX)

wherein R$^1$, R$^2$, R$^3$ and A are as defined above and R$^7$ represents a group convertable to an amino group by treatment with a reducing agent;

(f) in a compound of formula (X)

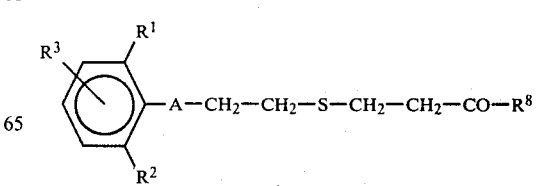
(X)

wherein R¹, R², R³ and A are as defined above and R⁸ represents —NH₂, —N₃ or —OH, converting the group COR⁸ into an amino group;

(g) reacting a compound of formula (XI)

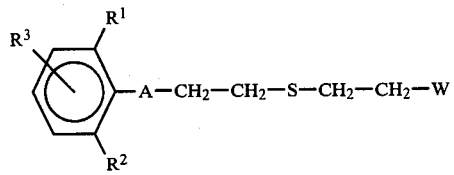

wherein R¹, R², R³, A and W are as defined above, either with ammonia, an amide or an imide, in which case any acyl group present is removed, or with hexamethylene tetramine, in which case the addition product is hydrolized.

In a compound of formula (XII)

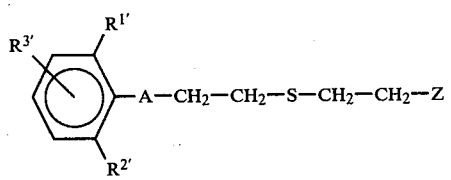

wherein A and Z are as defined above and R¹', R²' and R³' have the same meaning as R¹, R² and R³ respectively or signify hydrogen, at least one of R¹', R²' and R³' being hydrogen, introducing one or more of the groups R¹, R² and R³, and then, removing any amino protecting group present;

(i) In a compound of formula (XIII)

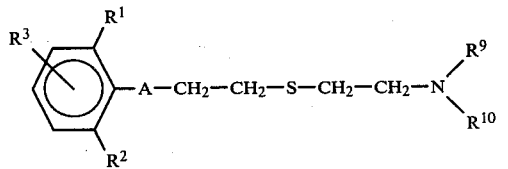

wherein R¹, R², R³ and A are as defined above and R⁹ and R¹⁰ represent hydrogen or an amino protecting group, at least one of R⁹ and R¹⁰ being such a group, removing the amino protecting group or groups.

Examples of preferred leaving groups W in the above starting materials are halogen or reactive esterified hydroxyl groups, such as arylsulphonic ester groups, phosphonic ester groups, and the like.

Examples of preferred functional groups R⁷ (formula IX), which can be reduced to a primary amino group, are —CH, —CH=NOH, —CONH₂, —CH=NH (aldehyde plus ammonia), —CH=NHNH₂ (which may be substituted with e.g. alkyl), and the like. The reduction can be carried in a manner known per se by treatment with reducing agents known to convert said groups R⁷ into an amino group. Examples of suitable reducing agents are complex metal hydrides such as lithium aluminium hydride, sodium borohydride, and the like, the reaction being carried out in an inert solvent such as ether, dioxan or tetrahydrofuran. Another suitable reducing agent is catalytically activated hydrogen gas, in which case the reaction is carried out in the presence of a catalyst such as a platinum, palladium or a nickel catalyst, preferably in a solvent such as water or a lower alcohol and at a hydrogen pressure from atmospheric pressure to 100 atm.

In several of the above described methods, the reactions can be carried out either with a free amino group or with the amino group being protected by means of a suitable protecting group, which is removed after the synthesis. A great variety of such protecting groups are well known to Chemists experienced in synthetic chemistry and can, for example, be removed by hydrolysis (acid or alkaline), hydrogenation, hydrazinolysis, etc., depending on the nature of the group.

When it is desired to produce the compounds of the invention in salt form, the salt may be prepared by reacting the free base form with the selected physiologically acceptable acid and, when R⁴ is H, with the selected physiologically acceptable base.

Where any selected starting materials necessary for preparing the compounds of formula I by methods described above are not previously reported in the literature, they can be prepared by analogy with known starting materials and/or by analogy with the methods described in the following Examples as for the production of starting materials.

The new compounds of formula (I) exhibit interesting pharmacodynamical properties. In particular, the compounds of formula (I) have an inhibitory effect on the fibron-stabilizing factor (Factor XII, fibrinoligase) in the blood, indicating their use in inhibiting the formation of thrombosis, treating thrombosis already formed and for supporting treatment in fibrinolytic therapy.

The factor XIII inhibiting activity of the compounds according to this invention is demonstrated in Table I below, dansylcadaverine and three parasubstituted benzene derivatives being included as reference substances. The strong activity increase caused by the introduction—according to the invention—of the substituents in the two orthopositions is evident when comparing compounds 5 and 6 with reference compound 2, compounds 7 and 8 with reference compound 3, and compound 9 with reference compound 4.

The test procedure used was the one described by Nilsson, Stenberg, Eriksson and Lunden in Acta Pharmaceutica Suecia 7, 441–448 (1970), the inhibition activity being expressed in % of that of dansylcadaverine.

TABLE I

STRUCTURE

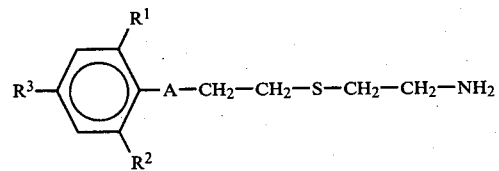

| Compound | R¹ | R² | R³ |
|---|---|---|---|
| 1.* | — | — | — |
| 2. | H | H | CH₃ |
| 3. | H | H | CH(CH₃)₂ |
| 4. | H | H | Cl |
| 5. | CH₃ | CH₃ | H |
| 6. | CH₃ | CH₃ | CH₃ |
| 7. | CH₃ | CH₃ | CH(CH₃)₂ |
| 8. | CH₃ | CH₃ | C(CH₃)₃ |
| 9. | Cl | Cl | H |
| 10. | C₂H₅ | C₂H₅ | H |
| 11. | CH₃ | CH₃ | NO₂ |
| 12. | CH₃ | CH₃ | CH₃ |

| Compound | A | Inhibiting Activity | |
|---|---|---|---|
| 1.* | — | 100 | |
| 2. | —SO₂NH— | 30 | reference |

TABLE I-continued

STRUCTURE

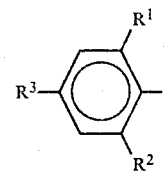

| | R¹ | | |
|---|---|---|---|
| 3. | " | 40 | substance |
| 4. | " | 20 | |
| 5. | " | 160 | |
| 6. | " | 200 | |
| 7. | " | 170 | |
| 8. | " | 170 | |
| 9. | " | 60 | |
| 10. | —NHSO₂— | 70 | |
| 11. | " | 90 | |
| 12. | —N(C₂H₅)—SO₂— | 150 | |

*Compound 1 is dansylcadaverine

The new compounds according to the invention can be formulated into pharmaceutical compositions by including the compound of formula I together with a pharmaceutically acceptable carrier. Conventional adjuvants may also be included. The compositions of the invention may be in solid or liquid form, e.g. tablets or solutions, preferably in dose unit form.

The invention also includes a method of inhibiting formation of thrombosis or treating existing thrombosis or in fibrinolytic therapy which comprises administering to a host in need of such treatment an effective amount of a compound of formula I, this amount is normally 5 mg to 2.5 g for adults but the exact amount will clearly depend upon the individual circumstances.

The following Examples are given to illustrate the invention.

EXAMPLE 1

(a) N-mesitylethene-sulphonamide 27.0 g (0.20 mole) mesitylamine were dissolved in 80 ml diethyl ether and mixed with 66.8 g (0.66 mole) triethylamine. The mixture was added dropwise to a stirred solution of 45.6 g (0.22 mole) bromoethylsulphochloride in 160 ml diethyl ether. The mixture was then refluxed for 5.5 hours and evaporated to dryness. The residue was treated with chloroform and 2 N hydrochloric acid and shaken. The chloroform phase was separated and extracted with 2 N sodium hydroxide solution. The alkaline aqueous phase was washed with chloroform, acidified with concentrated hydrochloric acid, and extracted with chloroform. The chloroform phase was dried over anhydrous magnesium sulphate and evaporated to dryness. 15.5 g of the crude title compound was obtained, which, after recrystallization from a mixture of di-isopropylether and hexane, melted at 117°–120° C.

In an analogous manner the following sulphonamide intermediates were obtained from the corresponding amines and bromoethylsulpochloride:
1. N-2,6-dimethylphenylethenesulphonamide; m.p. 84° C.
2. N-2,6-diethylphenylethenesulphonamide; m.p. 60° C.
3. N-2,6-diisopropylphenylethenesulphonamide; m.p. 108° C.

(b) N-mesityl-5-amino-3-thiapentanesulphonamide 1.6 g (0.077 mole) sodium were dissolved in 200 ml absolute ethanol to form a sodium ethoxide solution. 7.9 g (0.035 mole) N-mesitylethenesulphonamide and 2.7 g (0.035 mole) cysteamine were added to the ethoxide solution. The solution was allowed to stand at about 20° C. for 4 days and was then evaporated to dryness. The residue was treated with water, diethyl ether and 2 N hydrochloric acid and shaken. 1.4 g of unchanged starting material was obtained from the ether phase after drying. The aqueous phase was made alkaline with saturated sodium bicarbonate solution and was extracted with chloroform. The chloroform phase was dried over anhydrous potassium carbonate and evaporated to dryness yielding 10.0 g of crude amine. The crude product was dissolved in isopropanol, treated with HCl-diethyl ether and a large amount of di-isopropylether. 6.8 g of crude hydrochloride was obtained. After recrystallization from di-isopropylether/isopropanol, the title compound melted at 160° C. (hydrochloride).

In an analogous manner the following end products were obtained from the correspondingly substituted ethenesulphonamides and cysteamine:
1. N-2,6-dimethylphenyl-5-amino-3-thiapentanesulphonamide; hydrochloride, m.p. 175° C.
2. N-2,6-diethylphenyl-5-amino-3-thiapentanesulphonamide; hydrochloride, m.p. 112° C.
3. N-2,6-diisopropylphenyl-5-amino-3-thiapentanesulphonamide; m.p. 110° C. (free amine).

EXAMPLE 2

(a) N-mesityl-N-methylethenesulphonamide 22.5 g (0.1 mole) N-mesitylethenesulphonamide, 37.2 g anhydrous sodium carbonate, 52 ml methyl iodide and 1000 ml acetone were mixed and refluxed for 6 hours. The mixture was then filtered and evaporated to dryness. The residue was dissolved in diethyl ether and extracted with 2 N sodium hydroxide solution (to remove remaining starting material). The ether solution was dried over magnesium sulphate and evaporated to dryness. 24.0 g of the crude title compound was obtained as an oil, which solidifies slowly. M.p. c.a. 25° C.

In an analogous manner, using N-2,6-dimethylphenylethenesulphonamide and methyl iodide as starting materials, N-2,6-dimethylphenyl-N-methylethenesulphonamide; m.p. 50° C. was obtained:

(b) N-mesityl-N-methyl-5-amino-3-thiapentanesulphonamide 8.4 g (0.035 mole) of the product of Example 2a were reacted with 2.7 g (0.035 mole) cysteamine by the procedure described in Example 1b, yielding the title compound, m.p. 123° C. (hydrochloride).

In the same manner N-2,6-dimethylphenyl-N-methylethenesulphonamide and cysteamine were reacted to give N-2,6-dimethylphenyl-N-methyl-5-amino-3-thiapentanesulphonamide; m.p. 126° C. (hydrochloride).

EXAMPLE 3

(a) N-(2,6-dimethyl-4-nitrophenyl)-ethenesulphonamide

A solution of 12.6 g (0.06 mole) N-2,6-dimethylphenylethenesulphonamide, 120 ml concentrated acetic acid and 0.45 g sodium nitrite was slowly added to a mixture of 15 ml nitric acid and 120 ml water at 20°–25° C. The reaction mixture was refluxed for 2 hours and cooled to room temperature. Precipitation with 250 ml water gave an oil, which was extracted with CHCl₃, dried and evaporated to dryness. The title compound obtained melts at 132° C.

(b)
N-(2,6-dimethyl-4-nitrophenyl)-5-amino-3-thiapentanesulphonamide

The product obtained in Example 3a was reacted with cysteamine by the procedure described in Example 1b, to give the title compound; m.p. 159° C.

(c)
N-(2,6-dimethyl-4-aminophenyl)-5-amino-3-thiapentanesulphonamide 3.7 g (0.01 mole) of the product obtained in Example 3b were hydrogenated (Pd/C 10%, in concentrated acetic acid) at about 20° C. and 760 mm Hg for 3 hours. 675 ml H₂ were consumed. The catalyst was filtered off and the mixture was evaporated in vacuum, to give 3.7 g of the title compound, addition of HCl diethyl ether gave the di-HCl salt, melting at 216° C.

EXAMPLE 4

4-tert.butyl-2,6-dimethylbenzenesulphonylchloride 85 ml Chlorosulphonic acid (1.3 mole) was added to a mixture of 81 g (0.5 mole) 3,5-dimethyl-tert.-butylbenzene at 0±2° C. The reaction mixture was stirred at 0° C. for 1.5 hours, poured on ice and the layers were separated. The organic layer was washed with water, sodium bicarbonate, and water and was then dried with sodium sulphate. The solvent was removed in vacuum giving pale-yellow crystals of the title compound, m.p. 65° C.

EXAMPLE 5

2,4,6-trimethoxybenzenesulphonylchloride 16.8 g (0.1 mole) 1,3,5-trimethoxybenzene were added in portions to 33 ml chlorosulphonic acid, giving a clear pale-yellow solution. The solution was allowed to stand at about 20° C. for 2 hours and was then poured onto ice. The crystals formed were collected, washed with water, taken up in CHCl₃, washed with water, and dried with sodium sulphate. The solvent was removed in vacuum, giving 15 g of the crude title compound. The crude product was dissolved in a minimum of hot CHCl₃ and di-isopropylether was added. After cooling, white crystals of title compound (9 g) were collected; m.p. 134°–136° C.

EXAMPLE 6

2,6-dimethyl-4-nitrobenzenesulphonylchloride

A mixture of 13.6 g (0.082 mole) 2,6-dimethyl-4-nitroaniline, 80 ml concentrated HCl, and 6.3 g (0.09 mole) NaNO₃ was prepared at 0±2° C. and then stored in a cooler (5° C.) for 1.5 hours. The mixture was filtered and the precipitate was washed 3 times with small amounts of ice-water.

The aqueous filtrate was added to a mixture of 130 ml dioxane, 115 g SO₂, 60 ml benzene, 16 g MgCl₂.6H₂O, 8 g KCl and 14 g CuCl₂.2H₂O. The reaction mixture was stirred vigorously and gently warmed. When the temperature was at 20° C., gas evolution commenced, which became very vigorous at 30° C. Stirring was continued at 30°–40° C. for one hour, ice-water was added, and the layers were separated. The aqueous layer was extracted with CH₂Cl₂, and the combined organic layers were washed with cold brine, and dried with Na₂SO₄. After removal of the solvent in vacuum 14.5 g of the title compound was obtained as an oil, which crystallized at room temperature; m.p. 77° C. A sample recrystallized from petroleum ether containing a small amount of di-isopropyl ether melted at 82° C.

In an analogous manner, 2,6-difluorobenzenesulphonyl chloride was obtained as a reddish oil which was used without further purification.

EXAMPLE 7

N-(5-amino-3-thiapentyl)-mesitylenesulphonamide 6.6 g (0.03 mole) mesitylenesulphonyl chloride in 75 ml CH₂Cl₂ were added dropwise to a mixture of 30 ml 1,5-diamino-3-thiapentane, 150 ml CH₂Cl₂ and 6 ml triethylamine. The reaction mixture was stirred at about 20° C. overnight. After addition of Na₂CO₃ solution the mixture was washed with water and dried with Na₂SO₄. The solvent was removed in vacuum giving 10 g of white crystals of the title compound. Washing with petroleum ether and drying gave 8.4 g white crystals, which were recrystallized twice from di-isopropylether; m.p. 89.5°–93° C. The hydrochloride melted at 136.5°–139° C.

The following compounds were prepared by a similar procedure:

A. N-(5-amino-3-thiapentyl)-4-tert.-butyl-2,6-dimethylbenzenesulphonamide; m.p. 102° C.; fumarate m.p. 176° C.

B. N-(5-amino-3-thiapentyl)-2,6-dichlorobenzenesulphonamide; fumarate (bright yellow crystals), m.p. 160° C. approx.

C. N-(5-amino-3-thiapentyl)-2,4,6-trimethoxybenzenesulphonamide; fumarate m.p. 161° C.

D. N-(5-amino-3-thiapentyl)-2,6-dimethyl-4-nitrobenzenesulphonamide; m.p. 139° C., hydrochloride m.p. 205° C.

E. N-(5-amino-3-thiapentyl)-2,6-difluorobenzenesulphonamide; fumarate m.p. 170° C.

F. N-(5-amino-3-thiapentyl)-2,6-dimethylbenzenesulphonamide; white crystals m.p. 100° C.

G. N-(5-amino-3-thiapentyl)-2,4,6-triisopropylbenzenesulphonamide; white crystals m.p. 121° C., fumarate m.p. 168°–170° C.

H. N-(5-amino-3-thiapentyl)-2,6-dimethyl-4-isopropylbenzenesulphonamide; white crystals m.p. 99° C., fumarate m.p. 170° C.

I. N-(5-amino-3-thiapentyl)-3-chloro-2,6-dimethylbenzenesulphonamide.

EXAMPLE 8

N-(5-amino-3-thiapentyl)-4-amino-2,6-dimethylbenzenesulphonamide (dihydrochloride)

7.4 g (0.02 mole) of the product of Example 7D was hydrogenated over Raney nickel (2 spoons) in ethanol (200 ml). After 1160 ml H₂ had been absorbed (86% of the theoretical amount) no more H₂ was consumed. The reaction mixture was filtered and the filtrate was evaporated to dryness in vacuum, giving 6.3 g of salt. Water and an excess of 2 N HCl were added. The mixture was evaporated to dryness and the residue was dissolved in ethanol, filtered and cooled. The crystals were collected and washed with ethanol and ether, giving 5.8 g of white crystals of the title compound, m.p. 150°–160° C.

EXAMPLE 9

(a) N-(2-hydroxyethyl)-mesitylensulphonamide mesitylenesulphonate 84 g (0.4 mole) mesitylenesulphonyl chloride in 50 ml pyridine were added dropwise to a mixture of 12.2 g (0.2 mole) 2-aminoethanol and 20 ml pyridine at 0 ± 5° C. The reaction mixture was stored in a cooler (4° C.) overnight and then poured on ice. 30 ml acetic acid were added. The crystalline product was collected, washed with water and dried, giving 76 g of pale-yellow crystals of the title compound, m.p. 94° C.

(b) 6-(Mesitylenesulphonamido)-4-thiahexanoic acid 60 g (0.14 mole) of the product of Example 9a were added portionwise to 19 g (0.18 mole) 3-mercaptopropionic acid in 500 ml liquid ammonia and 8.3 g (0.36 mole) sodium. The reaction mixture was stirred at room temperature for about 2 hours until most of the ammonia had evaporated. The residue was dissolved in water, neutralized with acetic acid, acidified with concentrated HCl and extracted with diethyl ether. The ethereal solution was washed thoroughly with water, dried with $Na_2SO_4$, decolorized with carbon and filtered through Celite. The solvent was removed in vacuum giving 51.3 g of an oil, which rapidly solidified to a white crystalline mass. Washing with petroleum ether and drying gave 41.8 g of white crystals of the title compound, m.p. 80° C.

(c) 6-(Mesitylenesulphonamido)-4-thiahexanoyl chloride 4.8 g (0.0145 mole) of the acid of Example 9b was mixed with thionyl chloride and the mixture was allowed to stand at about 20° C. for 3 hours. Excess of $SOCl_2$ was removed in vacuum, giving 100% yield of a light brown oil, which NMR showed to be the title compound.

(d) N-(5-isocyanato-3-thiapentyl)-mesitylenesulphonamide 5.1 g (0.0145 mole) of the acid chloride of Example 9c in 10 ml acetone were cooled with ice-water. 1.0 g (0.0155 mole) sodium azide in 3 ml water were added dropwise and the solution was stirred for 0.5 hours. 20 g ice were added and stirring was continued for another 0.5 hours. The phases were separated and the aqueous phase was extracted with $CH_2Cl_2$. The organic phase was washed with ice-water and dried with $Na_2SO_4$. The solvent was removed in vacuum, giving a light brown oil. The azide was dissolved in 10 ml of sodium-dried benzene and the stirred solution was heated first at 40°–50° C., then at 80° C.

IR-spectrum showed a strong peak at 2270 cm$^{-1}$ and a weak one at 2140 cm$^{-1}$. The solution of the title compound was used in the next step without further purification.

(e) N-(5-amino-3-thiapentyl)-mesitylenesulphonamide

The isocyanate solution from Example 9d (0.0145 mole) was treated with pure concentrated hydrochloric acid whereupon gas evolution started. After it had subsided, the stirred mixture was warmed gently and then evaporated to dryness in vacuum. The residual brown oil was taken up in water and extracted with diethyl ether. The phases were separated and the aqueous phase was evaporated to dryness in vacuum, giving 3.3 g of a brown tacky product. This was dissolved in absolute ethanol, decolorized with active carbon and treated with a large amount of absolute diethyl ether. The crystals were collected, washed with diethyl ether and dried, giving beige crystals of the title compound. By IR and mixed m.p. the product was found to be identical with the product of Example 7.

EXAMPLE 10

(a) Bis-2-mesitylenesulphonamidoethyl disulphide 44 g (0.2 mole) mesitylenesulphonyl chloride in 500 ml $CH_2Cl_2$ at about 20° C. were added to 22.5 g (0.1 mole) cysteamine dihydrochloride in 500 ml water containing 18 g (0.45 mole) NaOH. The reaction mixture was stirred overnight and the organic layer was separated, washed with water, dilute hydrochloric acid and water, and dried with $Na_2SO_4$. The solvent was removed in vacuum, giving white crystals of the title compound, m.p. 140° C.

(b) N-(2mercaptoethyl)-mesitylenesulphonamide

A mixture of 20.7 g (0.04 mole) of the disulphide of Example 10a, 7.6 g (0.2 mole) $NaBH_4$, and 250 ml dioxane was heated to 90°–95° C. and stirred for 20 hours, then cautiously acidified with 20 ml 2N HCl and filtered. The filtrate was evaporated to dryness in vacuum, giving 21 g of a turbid oil. Recrystallization from di-isopropyl ether gave 16.6 g white crystals of the title compound, m.p. 73° C.

(c) N-(5-amino-3-thiapentyl)-mesitylenesulphonamide 2.6 g (0.01 mole) of the sulphonamide of Example 10b was mixed with 2 ml (about 0.04 mole) aziridine. The mixture was heated at 45°–50° C. for 2 hours. Excess of imine was removed in vacuum and the residual oil was leached with 3×5 ml hot di-isopropyl ether. The extract was taken to dryness in vacuum, giving 1.3 g of a semi-solid product. The crude product was recyrstallized from di-isopropyl ether giving 0.8 g white crystals of the title compound. IR and mixed m.p. showed that the product was identical with the compound of Example 7.

EXAMPLE 11

(a) N-(2-hydroxyethyl)-N-methylmesitylenesulphonamide mesitylenesulphonate 66 g (0.3 mole) mesitylenesulphonyl chloride in 37.5 ml pyridine were added dropwise at −5° C. to 11.2 g (0.015 mole) 2-methylaminoethanol. The reaction mixture was kept in a cooler (4° C.) overnight and then poured on ice. 20 ml acetic acid were added and the product was washed with water, taken up in diethyl ether, washed with water and dried with $Na_2SO_4$. The solvent was removed in vacuum, giving 55.7 g pale yellow crystals of the title compound, m.p. 94° C.

(b) N-(5-amino-3-thiapentyl)-N-methylmesitylenesulphonamide 17.6 g (0.04 mole) of the sulphonate of Example 11a were added to 3.1 g (0.04 mole) 2-aminoethanethiol and 0.92 g (0.04 mole) sodium in 170 ml ammonia. After addition of 15 ml dimethylformamide the mixture was stirred at room temperature until all ammonia had evaporated (about 1.5 hours). Diethyl ether and water were added and the layers were separated. The ethereal layer was washed with water and then extracted with 2N HCl. A white salt rapidly fell out from the HCl solution. The mixture was made alkaline with 2N NaOH and extracted with diethyl ether. The ethereal solution was washed with water and dried with $Na_2SO_4$. Removal of the solvent in vacuum 4.3 g of an oil. 4.0 g of the oil in $CH_2Cl_2$ were treated with an excess of ethereal HCl, giving 3.9 white crystals of the hydrochloride of the title compound, m.p. 165° C.

EXAMPLE 12

(a)

S-[2-(N-methylmesitylenesulphonamido)ethyl]-isothiouronium mesitylenesulphonate

A mixture of 20.5 g (0.047 mole) N-(2-hydroxyethyl)-N-methylmesitylenesulphonamide mesitylenesulphonate and 7.6 g (0.1 mole) thiourea in 100 ml absolute ethanol was stirred under gentle reflux for 60 hours and then cooled at about 20° C. The crystals formed were collected, washed with ethanol and dried, giving 23.3 g white crystals of the title compound, m.p. 202° C.

(b)

N-(4-cyano-3-thiabutyl)-N-methylmesitylenesulphonamide

A mixture of 23.2 g (0.045 mole) of the isothiouronium salt of Example 12a, 3.75 g (0.0495 mole) chloroacetonitrile, 1.4 g (0.0495 mole) sodium and 100 ml ethanol was stirred and refluxed gently for 2 hours, then cooled and filtered. The filtrate was taken to dryness, giving 14 g (100%) of a brown oil, which was dissolved in diethyl ether, washed with water, treated with active carbon and $Na_2SO_4$ and filtered. The solvent was removed in vacuum, giving 10.5 g of a pale pink oil. The oil was chromatographed on silica gel and eluted with methylene chloride, giving 7.5 g of a colorless turbid oil, which NMR showed to be the pure title compound.

(c)

N-(5-amino-3-thiapentyl)-N-methylemesitylenesulphonamide 3.6 g (0.023 mole) $AlCl_3$ in 50 ml absolute diethyl ether were added to 880 mg (0.023 mole) $LiAlH_4$ in 25 ml absolute diethyl ether. After 5 minutes 7.4 g (0.023 mole) of the cyano compound of Example 12b in 50 ml absolute diethyl ether were added dropwise. The mixture quickly clumped together, more ether was added, the clump was broken up mechanically and the mixture was allowed to stand at about 20° C. for 3 hours. The solution was poured off and the solid residue was washed with diethyl ether. The residual solid was taken up in $CHCl_3$ and the suspension was treated cautiously with water. Active carbon was added and the mixture was filtered through Celite. The layers were separated and the organic layer was dried with $Na_2SO_4$. Removal of the solvent gave 4.4 g crude product, which was washed with diethyl ether and recrystallised from absolute ethanol diethyl ether, giving 2.7 g white crystals of the hydrochloride of the title compound, m.p. 153°–155° C.

A further amount of the product was obtained from the original aqueous phase, which was made alkaline with solid NaOH, extracted with $CHCl_3$ and dried. Removal of solvent gave a pale-yellow oil, which was converted to the hydrochloride. 2.1 g white crystals, m.p. 151°–156° C.

EXAMPLE 13

(a)

N-(5-hydroxy-3-thiapentyl)-N-methylmesitylenesulphonamide 17.6 g (0.04 mole) N-(2-hydroxyethyl)-N-methylmesitylenesulphonamide mesitylenesulphonate were added to a mixture of 7.8 g (0.1 mole) 2-hydroxyethanethiol, 2.3 g (0.1 mole) sodium and 200 ml ammonia, and then 50 ml dimethylformamide were added, the reaction vessel being cooled in an acetone-$CO_2$ bath. The cooling bath was removed and the mixture was stirred at about 20° C. overnight. Water and diethyl ether was added and the aqueous phase was extracted with diethyl ether. The combined ether phases were washed with brine and dried with $Na_2SO_4$. Removal of the solvent in vacuum gave 12.3 g of an oil, which was used as such without further purification. NMR showed that it was the title compound.

(b)

N-(5-chloro-3-thiapentyl)-N-methylmesitylenesulphonamide 6.0 g (0.019 mole) of the hydroxy compound of Example 13a was mixed with 10 ml thionyl chloride. The mixture was allowed to stand at room temperature for 2 hours and then taken to dryness in vacuum. The residue was extracted with petroleum ether and decolourized with active carbon. Removal of the solvent in vacuum gave 5.8 g of the title compound as an oil.

(c)

N-methyl-N-(5-phthalimido-3-thiapentyl)-mesitylene sulphonamide

A mixture of 5.4 g (0.016 mole) of the chloro compound of Example 13b and 3.3 g (0.018 mole) potassium phthalimide in 20 ml dimethylformamide was stirred in a boiling water bath for 3.5 hours. After cooling, diethyl ether and water were added. The organic phase was washed with water, 0.4N NaOH, water and then dried. The solvent was removed in vacuum, giving 5.0 g of a viscous oil. Trituration with di-isopropyl ether and a small amount of methanol gave 1.5 g white crystals of the title compound, m.p. 95° C. Recrystallization from ethanol gave beige crystals, m.p. 104° C.

(d)

N-(5-amino-3-thiapentyl)-N-methylmesitylenesulphonamide

A mixture of 1.6 g (0.0036 mole) of the phthalimido compound of Example 13c and 0.2 ml (0.004 mole) hydrazine hydrate in 20 ml ethanol was stirred in boiling water bath for 2 hours and then taken to dryness in vacuum. The residue was stirred for 15 minutes with 10 ml 1:1 HCl in a water bath and then taken to dryness n vacuum. 10 ml water and active carbon were added. After filtration and evaporation to dryness in vacuum 1.1 g crude product was obtained, m.p. about 145° C. Recrystallization from ethanol gave beige crystals of the hydrochloride of the title compound, m.p. 155° C.

EXAMPLE 14

(a)

N-ethyl-N-(2-hydroxyethyl)-mesitylenesulphonamide mesitylenesulphonate 65.7 g (0.3 mole) mesitylenesulphonyl chloride in 37.5 ml pyridine were added to 13.4 g (0.15 mole) 2- ethylaminoethanol in 12.5 ml pyridine at 0° C. The mixture was left in a cooler (4° C.) overnight and then oured on ice. The syrup formed was washed with water and triturated with diethyl ether, whereupon it became crystalline. Petroleum ether was added. The product was collected, washed with diethyl ether/petroleum ether and dried, giving 45 g brown crystals of the title compound, m.p. 96° C. Recrystalization from 100 ml methanol gave 31.2 g white crystals, m.p. 98° C.

(b)
N-(5-amino-3-thiapentyl)-N-ethylmesitylenesulphonamide 27.1 g (0.06 mole) of the sulphonate of Example 14a were added to a mixture of 5.4 g (0.07 mole) 2-aminoethanethiol and 1.6 g (0.07 mole) sodium in 200 ml ammonia, followed by addition of 20 ml dimethylformamide. The reaction mixture was stirred at about 20° C. until all ammonia had evaporated (about 2 hours). The residue was dissolved in water and extracted with $CH_2Cl_2$. The extract was washed with water and dried with $Na_2SO_4$. Removal of the solvent in vacuum gave 19.7 g of a golden oil. NMR showed this oil to be the title compound, practically pure. Conversion to the fumarate gave white crystals, m.p. 160° C.

We claim:

1. A di-orthosubstituted benzene compound characterised in that it has the general formula (I)

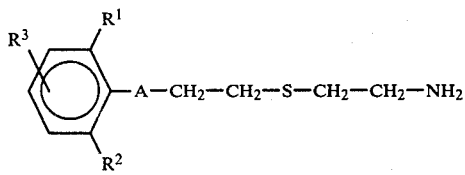

wherein $R^1$ and $R^2$ each independently represent an alky group containing 1 to 4 carbon atoms, or analkoxy group containing 1 to 3 carbon atoms, or halogen, $R^3$ represents hydrogen, halogen, an alkyl group containing 1 to 4 carbon atoms, an alkoxy group containing 1 to 3 carbon atoms, an amino group or a nitro group, A represents

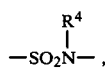

which is bonded to the benzene ring by its sulphur or nitrogen atom and in which $R^4$ is hydrogen or an alkyl group containing 1 to 4 carbon atoms; together with salts thereof with physiologically acceptable acids and, when $R^4$ is hydrogen, with physiologically acceptable bases.

2. A compound according to claim 1, wherein the sulphonamide group A is bonded to the benzene ring by its sulphur atom.

3. A compound according to claim 1 or 2, wherein $R^1$ and $R^2$ both represent methyl groups.

4. A compound according to claim 3, wherein $R^4$ is H.

5. A compound according to claim 3 wherein $R^3$ is H or a para methyl propyl or butyl group.

6. A compound according to claim 5 which is N-(5-amino-3-thiapentyl)-2,6-dimethylbenzene sulphonamide, or
N-(5-amino-3-thiapentyl)-2,4,6-trimethylbenzene sulphonamide, or
N-(5-amino-3-thiapentyl)-2,6-dimethyl-4-ispropylbenzene sulphonamide or
N-(5-amino-3-thiapentyl)-2,6-dimethyl-4-tert.-butylbenzene sulphonamide.

7. A compound according to claim 2 wherein $R^4$ is H.

8. A compound according to claim 2 wherein $R^3$ is H or a para methyl, propyl or butyl group.

9. A pharmaceutical composition comprising a compound or salt according to any one of claims 1, 2, 7 or 8 in an amount effective for inhibiting or combatting thrombosis or for supplementing fibronolytic therapy together with a pharmaceutically acceptable carrier.

10. A method or treatment for inhibiting formation of thrombosis or combatting thrombosis or supplementing fibrnolytic therapy which comprises administering to a host in need of such treatment a compound or salt according to any one of claims 1, 2, 7 or 8 in an amount effective for inhibiting formation of thrombosis or for combatting thrombosis or for supplementing fibronolytic therapy.

11. A pharmaceutical composition comprising a compound or salt according to claim 3 in an amount effective for inhibiting or combatting thrombosis or for supplementing fibronolytic therapy together with a pharmaceutically acceptable carrier.

12. A pharamaceutical composition comprising a compound or salt according to claim 4 in an amount effective for inhibiting or combatting thrombosis or for supplementing fibronolytic therapy together with a pharamaceutically acceptable carrier.

13. A pharmaceutical composition comprising a compound or salt according to claim 5 in an amount effective for inhibitng or combatting thrombosis or for suplementing fibronolytic therapy together with a pharmaceutically acceptable carrier.

14. A pharmaceutical composition comprising a compound or salt according to claim 6 in an amount effective for inhibiting or combatting thrombosis or for supplementing fibronolytic therapy together with a pharmaceutically acceptable carrier.

15. A method or treatment for inhibiting formation of thrombosis or combatting thrombosis or supplementing fibronolytic therapy which comprises administering to a host in need of such treatment a compound or salt according to claim 3 in an amount effective of inhibiting formation of trombosis or for combatting thrombosis or for supplementing fibronolytic therapy.

16. A method or treatment for inhibiting formation of thrombosis or combatting thrombosis or supplementing fibronolytic therapy which comprises administering to a host in need of such treatment a compound or salt according to claim 4 in an amount effective for inhibiting formation of thrombosis or for combatting thrombosis or for supplementing fibronolytic therapy.

17. A method or treatment for inhibiting formation of thrombosis or combatting thrombosis or supplementing fibronolytic therapy which comprises administering to a host in need of such treatment a compound or salt according to claim 5 in an amount effective for inhibiting formation of thromobosis or for combatting thrombosis or for supplementing fibronolytic therapy.

18. A method or treatment for inhibiting formation of thrombosis or combatting thrombosis or supplementing fibronlytic therapy which comprises administering to a host in need of such treatment a compound or salt according to claim 6 in an amount effective for inhibiting formation of thrombosis or for combatting thrombosis or for supplementing fibronolytic therapy.

* * * * *